United States Patent
Breuer et al.

(10) Patent No.: US 9,547,333 B2
(45) Date of Patent: Jan. 17, 2017

(54) SYSTEM AND METHOD FOR SYNCHRONIZING NETWORKED COMPONENTS

(71) Applicant: GENERAL ELECTRIC COMPANY, Schenectady, NY (US)

(72) Inventors: Brian Breuer, Waukesha, WI (US); Steven John Woloschek, Waukesha, WI (US); Nathanael Dale Huffman, Waukesha, WI (US); Eric Aasen, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 430 days.

(21) Appl. No.: 14/051,137

(22) Filed: Oct. 10, 2013

(65) Prior Publication Data

US 2015/0106645 A1    Apr. 16, 2015

(51) Int. Cl.
| | |
|---|---|
| G06F 1/04 | (2006.01) |
| G06F 1/12 | (2006.01) |
| A61B 6/03 | (2006.01) |
| H04J 3/06 | (2006.01) |
| A61B 6/00 | (2006.01) |

(52) U.S. Cl.
CPC ............... *G06F 1/12* (2013.01); *A61B 6/032* (2013.01); *A61B 6/566* (2013.01); *G06F 1/04* (2013.01); *H04J 3/0658* (2013.01)

(58) Field of Classification Search
CPC ..................................... G06F 1/04; G06F 1/12
USPC ....................................................... 713/400
See application file for complete search history.

(56) References Cited

U.S. PATENT DOCUMENTS

| | | | |
|---|---|---|---|
| 3,790,892 A | | 2/1974 | Tan et al. |
| 4,157,472 A | | 6/1979 | Beck, Jr. et al. |
| 4,513,427 A | | 4/1985 | Borriello et al. |
| 5,696,505 A | | 12/1997 | Schouhamer Immink |
| 5,907,253 A | * | 5/1999 | Davis ............... H03L 7/081 327/156 |
| 6,028,903 A | | 2/2000 | Drost et al. |
| 6,591,283 B1 | * | 7/2003 | Conway ........... G11B 20/10009 360/46 |
| 7,940,129 B1 | | 5/2011 | Tsang et al. |
| 8,259,758 B2 | * | 9/2012 | Chen ..................... H04J 3/0667 370/503 |
| 8,295,423 B2 | | 10/2012 | Hajimiri et al. |
| 8,307,235 B2 | * | 11/2012 | Patel ..................... G06F 1/12 713/400 |

(Continued)

OTHER PUBLICATIONS

RapidIO; RapidIO Technology Solves the Communications Fabric Conundrum, Rapidfabricwp, Sep. 2005.

(Continued)

*Primary Examiner* — Chun Cao
(74) *Attorney, Agent, or Firm* — Grogan, Tuccillo & Vanderleeden, LLP

(57) ABSTRACT

A method for synchronizing a plurality of components that are networked via a plurality of high speed switches, the method includes frequency-locking to a master clock component clocks of the plurality of components, and synchronizing to a master counter, driven by the master clock, component counters of the plurality of components, so that the frequency-locked component clocks drive the component counters in synchrony with the master counter.

4 Claims, 4 Drawing Sheets

(56) References Cited

U.S. PATENT DOCUMENTS

| | | | |
|---|---|---|---|
| 2007/0260906 A1* | 11/2007 | Corredoura | G06F 1/12 |
| | | | 713/400 |
| 2010/0085090 A1 | 4/2010 | Lin et al. | |
| 2012/0008727 A1 | 1/2012 | Mohajeri et al. | |
| 2013/0034197 A1* | 2/2013 | Aweya | H04J 3/0664 |
| | | | 375/362 |

OTHER PUBLICATIONS

RapidIO; Technology Overview and Applications; Technical Discussion of the RapidIO Interconnect and System Design Examples; May 2005.
Jeff Feigin; Practical Costas Loop Design; RF Signal Processing; Jan. 2002.
RapidIO; The Embedded Fabric Choice.
RapidIO; Synopsis of the Data Streaming Logical Specification (Phase I); Sep. 2005.
Jiang Wu and Robert Peloquin; Synchronizing Device Clocks Using IEEE 1588 and Blackfin Embedded Processors; Nov. 2009.
P. Lutus; Understanding Phase-Locked Loops; 2011.
International Telecommunication Union; Series G: Transmission Systems and Media; Definitions and Terminology for Synchronization Networks; Aug. 1996.
J.B. Berner, et al.; Flexible Loop Filter Design for Spacecraft Phase-Locked Receivers.
Dan Hu; FPGA-Based Digital Phase-Locked Loop Analysis and Implementation; Thesis; University of Illinois at Urbana-Champaign, 2011.

* cited by examiner

SYSTEM AND METHOD FOR SYNCHRONIZING NETWORKED COMPONENTS

TECHNICAL FIELD

Embodiments of the invention relate generally to time synchronization of networked components. Particular embodiments relate to time synchronization of CT scanner subsystems and computer equipment.

DISCUSSION OF ART

CT scanners are used in medicine both for diagnosis and for guidance of interventions. In a CT scanner, an X-ray source and a detector (such as an array of scintillation crystals with associated photomultipliers or photodiodes) are positioned opposite each other on a gantry, which rotates around a target such as a patient. The X-ray source is activated to emit X-rays, some of which pass through the target and others are reflected or absorbed by the target. X-rays that pass through the target to the detector generate signals.

The signals at the detector vary temporally due to stochastic fluctuations in absorption and reflection of the X-rays, and also vary spatially as the source and detector rotate around the stationary target, which thereby presents different absorption and reflection characteristics at each angular position of the gantry. The variations of the detector signals, during one or more rotations of the gantry, can be mathematically correlated or "computed" in a central processing unit, which generates correlation data suitable for producing a cross-sectional image representation of different types of tissue or other material within the target.

Computer processors are known for implementing software, e.g., the algorithms necessary for operation of a computed tomography (CT) scanner components to emit and detect X-rays and to correlate detections with gantry positions and with source position relative to the target. Computer processors implement software instructions by switching electronic logic gates to manipulate binary HIGH or LOW signals ("bits"). Computer processors can be implemented in RISC, ASIC, FPGA, or other architectures.

Accuracy of correlation, and, consequently, image quality, depend to a great extent upon accurate logging of the X-ray source and detector positions relative to the target. Typically, these positions are calculated based on elapsed time from a zero-time reference position, and based on measurements of gantry angular velocity derived from, e.g., a time integral of gantry motor current, voltage, or shaft speed. Alternatively, positions may be directly measured from a bar code or the like marked on a surface of the gantry. In any case, each detector signal and each position reading typically is tagged with the local time at the detector or position sensor, and for enhanced quality, the X-ray source power level also may be continuously or periodically measured and tagged with the local time at the source. Thus, timekeeping is a critical aspect of CT scanner design.

In complex systems like CT scanners, multiple processors are networked together. For example, a CT scanner may include an X-ray source processor, an X-ray detector processor, a position sensor processor, and a gantry control board processor, all of these being configured for communication with each other via a network. Typically, networked processors communicate with each other by sending data packets. For coordinated action, networked processors attempt to maintain synchrony so that each received data packet is implemented or passed on in proper sequence. Each processor has its own clock (comprising a time counter driven by an oscillator, e.g., a bistable), and synchrony can be maintained by periodically transmitting and receiving a time signal, from a designated "master" clock to the "slave" clocks of the other processors. The component clocks periodically adjust their time counters in response to the time signals received from the master clock. Between time signals, the component clocks increment their time counters based on the pulses produced by their respective oscillators.

The master clock/time signal paradigm is often employed because it is data-efficient and has low network overhead. Typical periodicities for master clock time signals range from about 1 MHz to about 200 MHz and each processor switches its logic gates anywhere from about 1000 times to about 5 times between receipt of each time signal from the master clock. As a result, a large quantity of process data can be generated and transmitted between time signals, using the same signal path used for the time signals ("path sharing"). By contrast, continuous synchronous network time protocols (continuous time signal transmissions) are not favored because such protocols require a dedicated physical layer that cannot also be used for transmitting process data.

A potential issue with the time signal paradigm is that, during the numerous switching operations between time signals while the component clocks increment their respective time counters, asynchrony or clock "drift" can emerge between the master clock and each component clock and also among the component clocks. The clock drift phenomenon arises because each component clock oscillator has its own characteristic frequency that infinitesimally varies from the frequencies of the other clock oscillators. Over an extended sequence of switching operations, the different frequencies of the different oscillators can result in significant divergence of the component clock time counters.

Another potential issue with the time signal paradigm is that a unique network transit time or signal delay exists between the master clock and each component clock. Accordingly, each component clock receives the time signal at a different time relative to the master clock. This time difference can change according to environmental factors that can vary the transmission delay. Some possibly relevant environmental factors include, for example, thermal strain, changes in impedance, electromagnetic field interactions. The ordinary expected result of this variation in transit time is that each component clock time "jitters" around the master clock time.

For example, image quality of a CT scanner can be limited by "clock drift" or "jitter" between the processors associated with the detector, the source, the position sensor, and the gantry control board. In particular, variance of detector local time away from source or position sensor local time, or from gantry control board local time, can result in erroneous position readings, which limit the achievable quality of the correlation data. Depending on the error threshold designed into the particular CT scanner, small clock drifts can degrade image quality without establishing an error condition.

IEEE 1588 improves on the time signal paradigm by implementing a Best Master Clock (BMC) algorithm that is run by all of the processors, in order to select which processor will run the master clock. One feature of the BMC algorithm is that the processors cooperatively select a master clock in a manner that is not necessarily determinative from a user standpoint—in other words, the BMC algorithm is not intended to "force" selection of any particular processor as the master clock.

IEEE 1588 addresses an issue of component clock drift due to component clock oscillator frequency differing from master clock oscillator frequency by instituting a reciprocal measure of time signal delay. The reciprocal measure of time signal delay is used by each component clock for adjusting its local time from the time of receiving the master clock pulse, to more closely approximate the simultaneous local time at the master clock. Determining the reciprocal measure of time signal delay, for each component clock, requires repeated reciprocal communication at scheduled intervals between the master clock and the component clocks.

BRIEF DESCRIPTION

An aspect of the invention provides a method for synchronizing a plurality of components that are networked via a plurality of high speed switches. The method comprises frequency-locking to a master clock the component clocks of the plurality of components, and synchronizing to a master counter, driven by the master clock, a plurality of component counters driven by the plurality of component clocks, so that the frequency-locked component clocks drive the component counters in synchrony with the master counter.

In another embodiment, a method is provided for frequency-locking a component clock to a master clock. The method comprises defining a clock frequency and a master counter by periodically providing a master clock pulse from the master clock to a clock encoder; in the clock encoder, modulating the master clock pulse onto a serial data stream that has a bit transition rate greater than the clock frequency; and transmitting the clock stream from the clock encoder to a clock decoder portion of the component clock, which recovers clock pulses from the clock stream.

Embodiments of the invention provide a synchronous network time system, which comprises a master clock configured to generate a sequence of master clock pulses at a clock frequency; a master processor configured to receive the master clock pulses, maintain a master counter of the master clock pulses, and generate a serial data stream including instructions for initializing a component counter; a clock encoder configured to receive the serial data stream and the master clock pulses, and generate a clock stream by modulating the master clock pulses onto the serial data stream; a clock decoder configured to receive the clock stream, and extract from the clock stream the serial data stream and a sequence of component clock pulses; and a component clock configured to initialize and maintain a component counter based on the instructions from the master processor and the component clock pulses.

Moreover, a technical effect of the invention is to provide "zero overhead" modes of synchronizing networked components. As used herein, the term "zero overhead" refers to methods and systems for synchronizing networked components that do not require repeated discrete time signals or a dedicated channel for continuous time signaling (once originally synchronized).

DRAWINGS

The present invention will be better understood from reading the following description of non-limiting embodiments, with reference to the attached drawings, wherein below:

DETAILED DESCRIPTION

Figure 1:
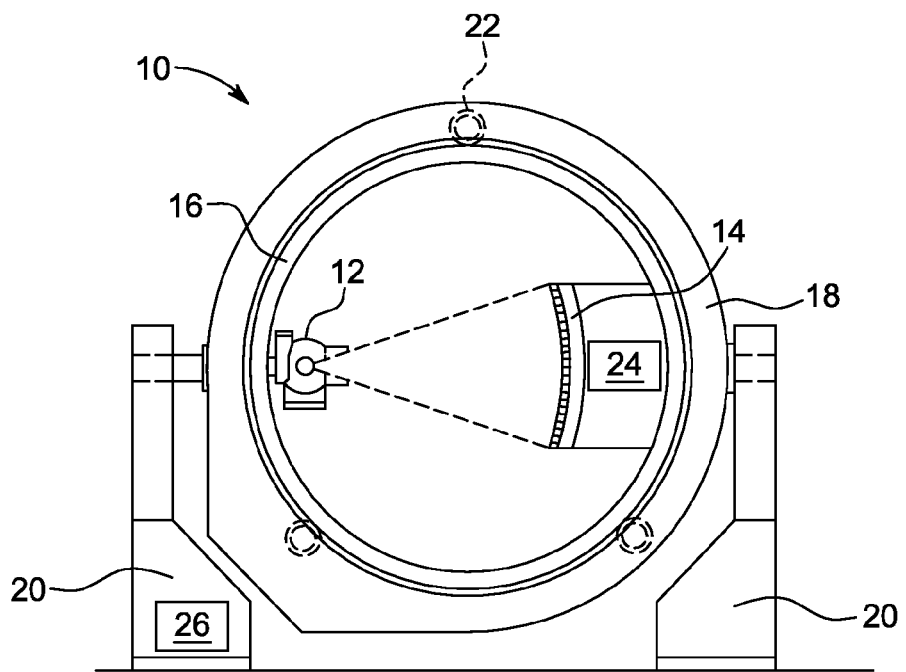
FIGS. 1 and 2 are front and side elevation views of a conventional CT scanner.

Reference will be made below in detail to exemplary embodiments of the invention, examples of which are illustrated in the accompanying drawings. Wherever possible, the same reference characters used throughout the drawings refer to the same or like parts, without duplicative description.

Aspects of the invention relate to driftless synchronization of multiple clocks implemented in digital circuitry. Although exemplary embodiments of the present invention are described with respect to a CT scanner that includes a gantry control board and plural gantry components mounted on a gantry within a stationary frame, embodiments of the invention also are applicable for use with networked time systems, in general. Networked time systems may be found, for example, in engine controllers for automotive, off-highway, marine, or rail vehicles, as well as in power generation and distribution systems.

Figure 2:
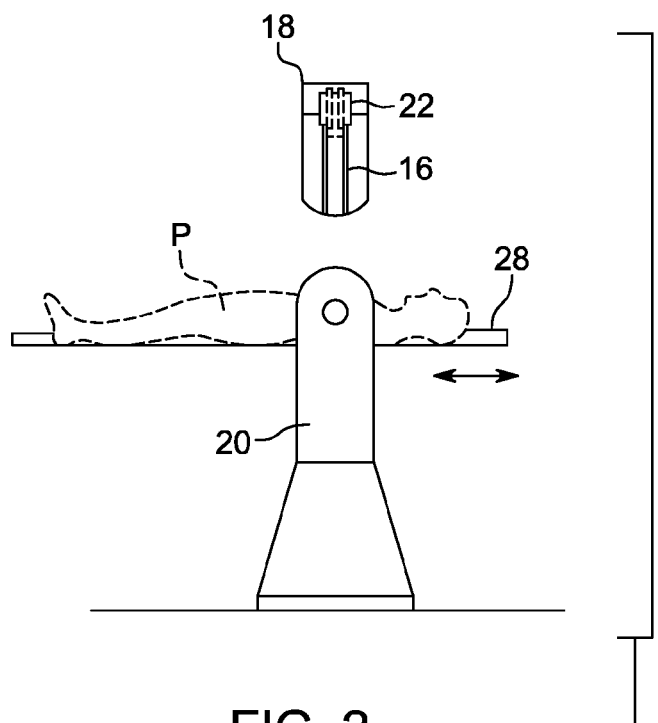

Referring to FIGS. 1 and 2, CT scanners 10 typically include a source 12 and a detector 14, which are supported on a rotating gantry 16. The gantry is supported in a frame 18, which is pivotally mounted on supports 20. The gantry 16 is rotatable within the frame 18 by plural motor-driven wheels 22, which may be mounted on the gantry or on the frame. The source 12, the detector 14, and the motor-driven wheels 22 (collectively, "gantry components") each are controlled by processors that implement instructions transmitted from a gantry control board ("master endpoint") 24, which in turn is configured to implement instructions transmitted from a system controller 26.

CT scanners 10 further include a table 28, which is configured and disposed to be longitudinally movable generally parallel to the axis of rotation of the gantry 16. The table 28 is operated separately from the gantry components, typically under control of the system controller 26.

In use, a patient P is positioned on the table 28 within the gantry 16, and the gantry control board 24 operates the wheels 22 to rotate the gantry around the patient. As the gantry 16 rotates, the gantry control board 24 also operates the source 12 and the detector 14. The gantry control board 24 correlates time-stamped detector data with time-stamped gantry position data, thereby obtaining scan data, which the gantry control board then passes to the system controller 26. Simultaneously, the system controller 26 operates the table 28 to either continuously or stepwise move the patient P along the gantry rotational axis, and receives time-stamped table position data. The system controller 26 correlates the table position data with the scan data from the gantry control board 24 to generate either a set of one or more "slice" scans closely spaced along the patient, or a continuous "spiral" or "helical" scan around and along the patient. The system controller 26 then transmits the scan or scans to an off-board processing unit (not shown), which produces viewable scan images as well as a 3-D model of the patient.

As discussed above, a longstanding issue in CT scanning technology is that clock drift, among the gantry components and the gantry control board 24, can potentially degrade the accuracy of the scan data. Additionally, clock drift between the gantry control board 24 and the system controller 26 can potentially degrade the accuracy of the scan images and of the 3-D model.

Figure 3:
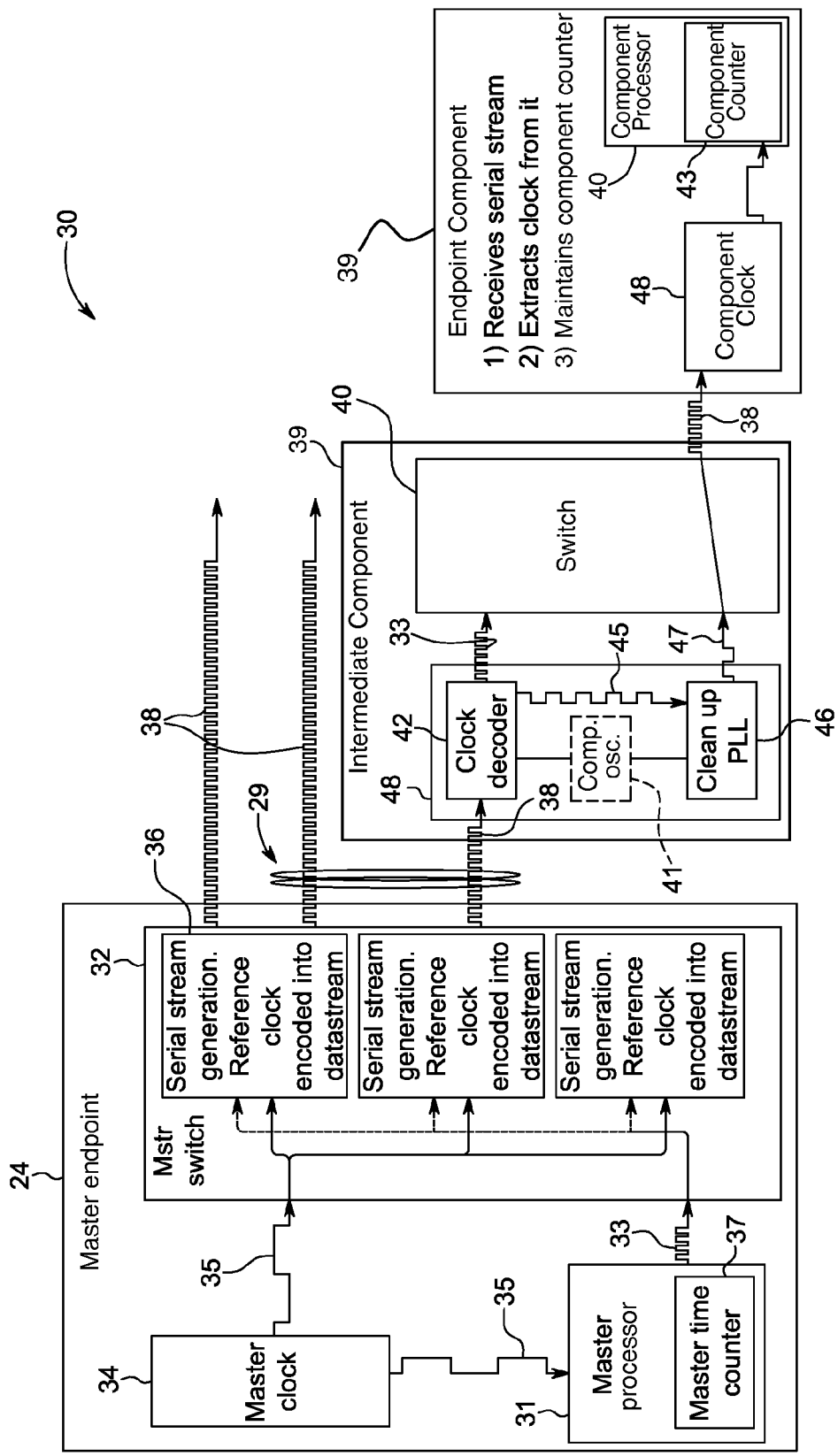
FIG. 3 shows in schematic view a mode of clock frequency communication, according to one aspect of the present invention.

Referring now to FIG. 3, it has been typical that the gantry control board 24 communicates with at least one of the gantry components 14, 16, 22 or the system controller 26 via electrical contact between a pair of slip rings 29 (shown schematically in FIG. 3), which are disposed on the gantry 16 and on the frame 18. In any case, according to aspects of the present invention, a synchronous network time system 30 is implemented to frequency-lock all the components to a master clock frequency of the gantry control board, and thereby eliminate clock drift among the gantry control board and the gantry components.

In order to support clock frequency communication or "frequency-locking," as shown by FIG. 3, the gantry control board (more generally, "master endpoint") 24 includes a master processor 31, a master switch 32, a reference oscillator or "master clock" 34, a clock encoder 36, and a master counter 37 that is maintained in the master processor 31. The master processor 31 is a processor, e.g., an ASIC, FPGA, or conventional processor (typically operating at a relatively high instruction throughput, e.g., 8 gigaflops or higher) that generates a relatively high speed serial data stream (the "master stream" 33) encoding instructions for operation of subordinate components. The master switch 32 is, by way of example without limitation, a switch compliant with the Serial Rapid IO standard. In certain embodiments, the master switch 32 is capable of handling a data throughput of, e.g., at least about 1 Gb/sec. (As used herein, the terms "substantially," "generally," and "about" indicate conditions within reasonably achievable manufacturing and assembly tolerances, relative to ideal desired conditions suitable for achieving the functional purpose of a component or assembly.) The master clock 34 is connected in communication with the master switch 32 and the master processor 31 to provide both devices a "master clock pulse" 35 at a pre-determined clock frequency, e.g., in some embodiments between about 60 MHz and about 270 MHz, or in other embodiments between about 100 MHz and about 180 MHZ, or in certain embodiments about 125 MHz. Other data rates and frequencies may be used. The clock encoder 36, typically implemented within the master switch 32, but also implementable in a separate device, e.g., an FPGA, an ASIC, a generic processor appropriately configured by software, or the like, encodes the master clock pulse 35 onto the master stream 33, thereby producing a clock stream 38 that is outgoing from the master endpoint 24 to subordinate components 39. The subordinate components 39 may include "endpoint" components (e.g., the source 12 or detector 14) as well as "intermediate" components (e.g., a second switch similar to the master switch 32). Each of the subordinate components 39 includes a processor 40, which may be configured to accomplish a particular function (e.g., controlling the source 12 or the detector 14) or simply to route data (e.g., a second switch as mentioned above).

Therefore, while the CT scanner 10 is operating, the master processor 31 continually generates the master stream 33, which includes a pattern of bit transitions at relatively high data rate (e.g., from about 2.5 G/bs up to about 5 Gb/s, or typically 10× to 20× the reference clock rate). The master stream 33 includes instructions from the master processor 31 to each of the various component processors 40. The clock encoder 36, which is implemented in the master switch 32, encodes each master clock pulse 35 into the master stream 33 in order to produce the clock/data stream 38.

Meanwhile, each of the components 39 includes a processor 40, an oscillator 41, a clock decoder 42, and a cleanup phase-locked-loop ("PLL") 46. Each of the components receives from the master endpoint 24, at its respective clock decoder 42, the clock stream 38, which encodes the master clock pulse 35. The clock decoders 42 receive and demodulate the inbound clock stream 38 in order to reproduce the master stream 33 and in order to obtain demodulated or decoded clock pulses 45. Each clock decoder 42 passes the demodulated master stream 33 directly to the component processor 40. Because the demodulated clock pulses 45 may include some artifacts of modulation/demodulation, e.g., partial phase shifts, spurious signal level changes, or other noise attributable to encoding, transmission, and decoding of the clock pulse (collectively, "jitter"), the clock decoder 42 passes the demodulated clock pulses 45 to the component processor 40 via the PLL 46, which removes the jitter to produce a component clock pulse 47. The PLL 46 then passes the component clock pulse 47 to the component processor 40, and back into the clock decoder 42. In view of the above, the clock decoder 42, and the PLL 46, together form a component clock 48 that is driven by the clock stream 38. In other words, once the component has started up, the clock stream 38 replaces the component oscillator 41.

In case one of the components 39 is an "intermediate" component (i.e., a switch), the processor 40 is configured to simply encode the component clock pulses 47 back onto the extracted master stream 33, thereby producing an outbound copy of the clock stream 38. On the other hand, in case another of the components 39 is an "endpoint" component, then the component processor 40 implements a component counter 43 that is driven (incremented) by the component clock pulses 47 from the component clock 48 in order to indicate local time at the component.

Under the conventional "time signal" paradigm, every component would be operated such that its respective oscillator 41 would increment a component counter, which would be periodically adjusted based on a time signal sent from a master clock. By contrast, according to aspects of the present invention, the master clock 34 and the component clocks 48 together form a global time keeping system that transparently synchronizes the master and component counters 37, 43 without requiring repeated broadcasts of discrete time signals or a discrete channel for continuous time signal communication. Thus, embodiments of the invention provide a "zero overhead" paradigm for synchronization of networked component clocks.

Figure 4:
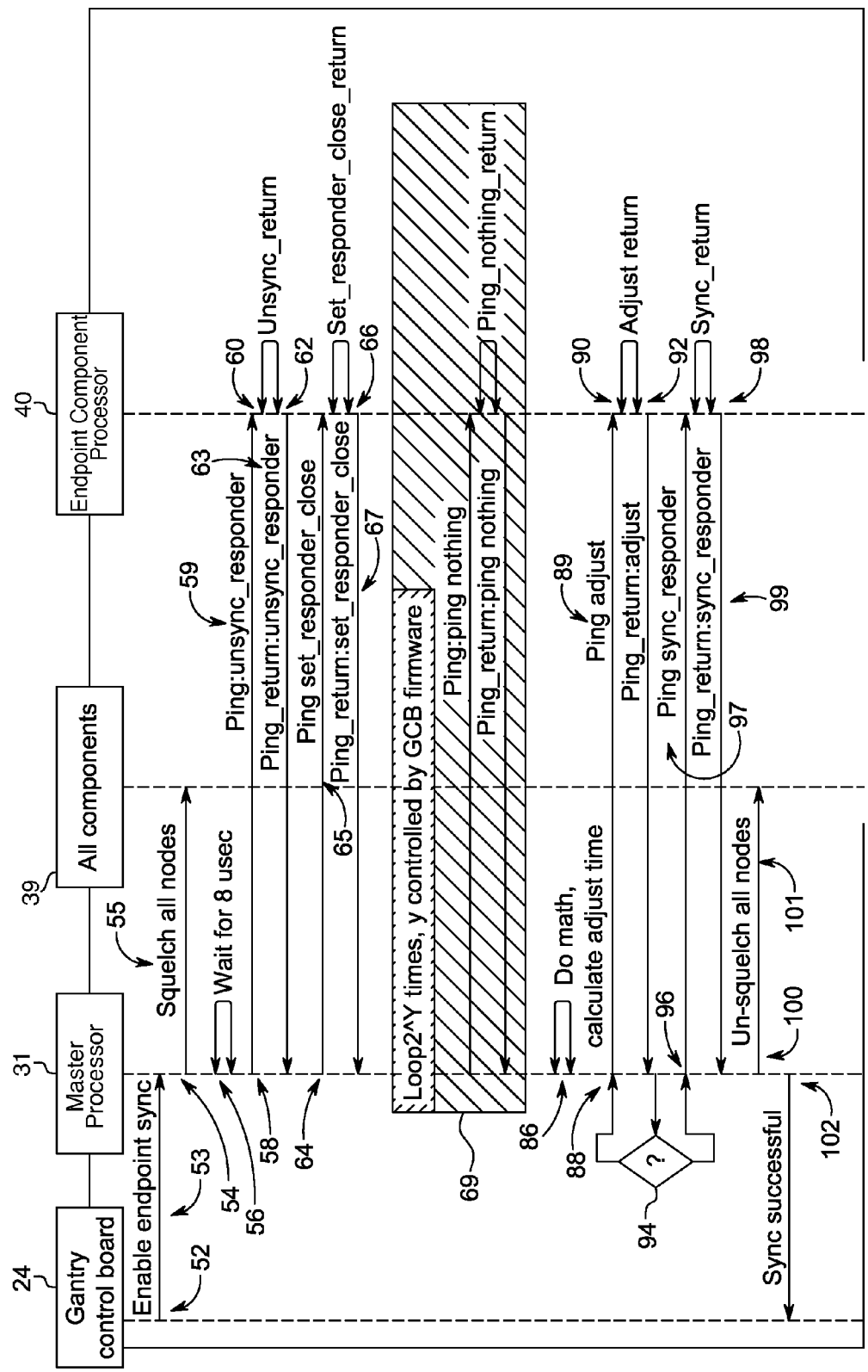
FIG. 4 shows in schematic view a process for clock synchronization, according to one aspect of the present invention.

FIG. 4 shows in schematic view a sync process 50 that the master processor 31 and the endpoint component processors 40 implement for initializing the component counters 43 in synchrony with the master counter 37. This sync process 50 is performed at each system startup, and on detection of a newly-connected endpoint component. In the sync process 50, the master endpoint 24 inserts 52 into the master stream 33 an instruction 53 to "enable endpoint sync." In response to the instruction 53, the master processor 31 sends 54 an instruction 55 to "squelchallnodes." This causes all receiving components to suspend normal operations until the time synchronization process 50 has finished (or, optionally, until expiry of internal timers).

The master processor 31 waits 56 for a pre-determined time, then sends 58 a packet 59 "unsyncresponder." Each endpoint component processor 40 receives 60 "unsyncresponder," and accordingly, zeroes or clears or otherwise desynchronizes its associated component counter 43. Then, each endpoint component processor 40 returns 62 a packet 63 "returnunsyncresponder." After receiving "unsyncresponder" back from all the endpoint component processor 40, the master processor 31 sends 64 a ping packet 65 "setresponderclose," which encodes a time of sending from the clock encoder. Each endpoint component processor 40 receives "setresponderclose" and sets 66 its component counter 43 to the encoded time of sending.

Figure 5:
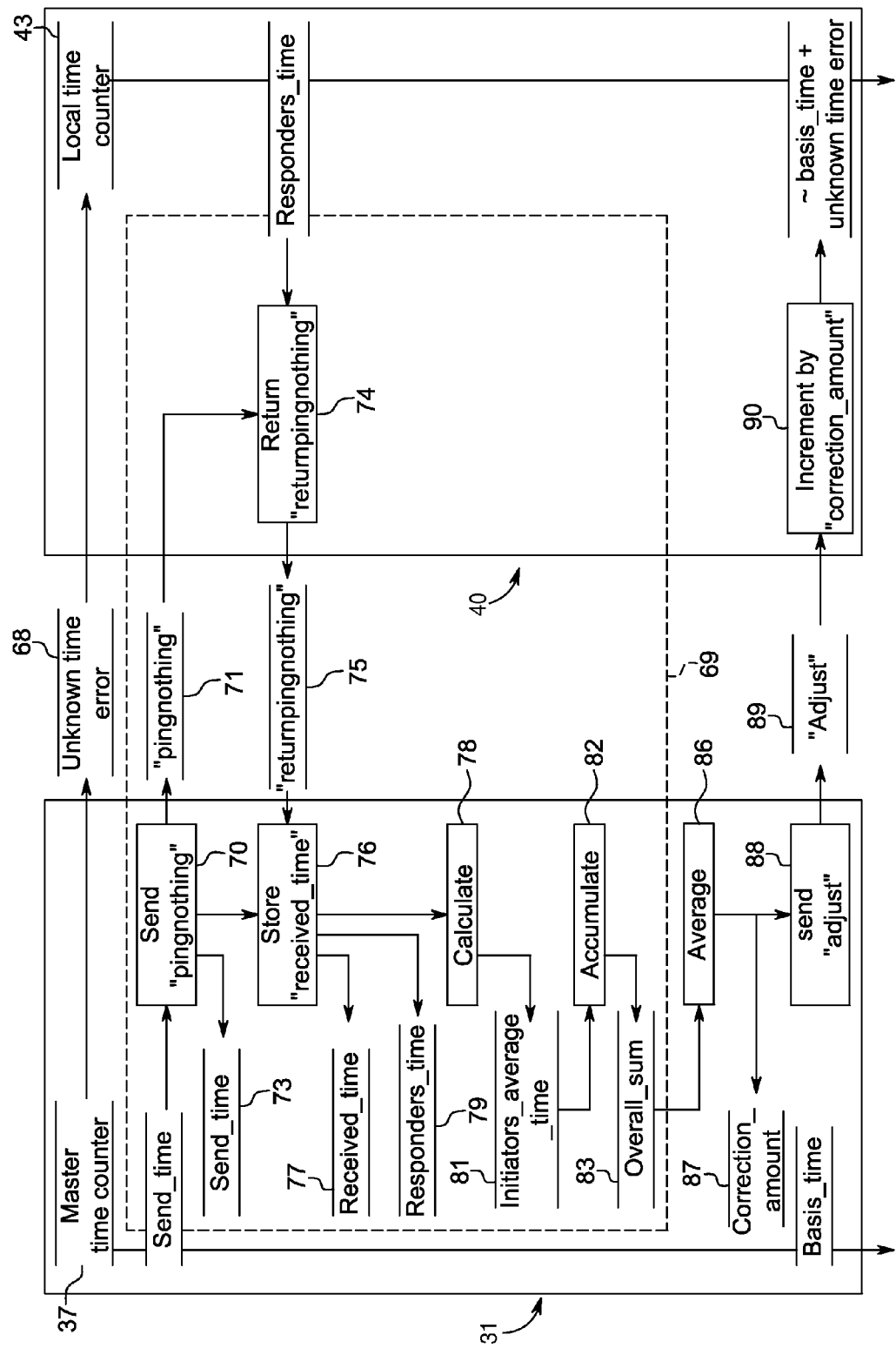
FIG. 5 shows in schematic view details of steps for determining clock errors, according to the process of FIG. 4.

Referring to FIG. 5, each endpoint component processor 40 now has its component counter 43 set to a value that lags the master counter 37 by an unknown time error 68. Thus, the master processor 31 begins to determine 69 the plurality of time errors 68, each corresponding to one of the clock decoders 42, so that the component counters 43 can be set to better approximate the master counter 37. Repeatedly, the master processor 31 sends 70 to each endpoint component processor 40 a "pingnothing" packet 71, and stores the time of sending "pingnothing" as "send_time" 73. Each endpoint component processor 40 returns 74 "returnpingnothing" packet 75, which encodes a time of sending from the endpoint component processor 40 as obtained from the associated component counter 43. Typically, and on average, the time of sending encoded in "returnpingnothing" 75 will match the receipt time at which the clock decoder received "pingnothing" 71. The master processor 31 stores 76 its time of receiving "returnpingnothing" as "received_time" 77, and the clock decoder time of sending as "responders_time" 79. In view of the above, "receipt time" as used herein refers to the times that the clock decoder receives "pingnothing" 71.

The master processor 31 then calculates 78 an average of "send_time" and "received_time," and stores the calculated value as "initiators_average_time" 81, which is the time that a perfectly synchronized clock decoder would have returned as its "responders_time." Additionally, the master processor 31 accumulates 82, for each endpoint component processor 40, a running total or "overall_sum" 83 of the time errors between "responders_time" and "initiators_average_time."

After iterating "n" times through determining 69 the time errors 68, the master processor 31 averages 86 the "overall_sum" for each endpoint component processor 40 to generate a "correction_amount" 87 for each clock decoder. Now that the "correction_amount" has been determined for each endpoint component processor 40, the master processor 31 then sends 88 to each endpoint component processor 40 an "adjust" packet 89, which encodes the "correction_amount" 87 for setting the component counter 43 to match the master counter 37. Each endpoint component processor 40 increments 90 its component counter 43 according to the "correction_amount," thereby setting the component counter 43 approximately equal to a "basis_time" at which the "adjust" packet 89 was sent, plus the "correction_amount."

Referring again to FIG. 4, each endpoint component processor 40 then returns 92 a "returnadjust" packet 93 indicating the time value of the updated component counter 43. The master processor 31 checks 94 whether the "returnadjust" packet time substantially matches the master counter 37 minus the "correction_amount." (In certain embodiments, the step of checking 94 may allow for various tolerances around the exact match; e.g., plus or minus several clock pulses, one microsecond, one millisecond, or one one hundredth of a second). If so, then the master processor 31 sends 96 a "syncresponder" packet 97, which confirms to the endpoint component processor 40 that its component counter 43 is correctly set. If not, then the master processor 31 sends 88 another "adjust" packet 89. Once all the clock decoders 42 have acknowledged 98 their respective "syncresponder" packets by sending "returnsyncresponder" packets 99, the master processor 31 sends 100 a packet 101 "unsquelchallnodes," which releases the receiving components to continue their normal operations. The master processor 31 also reports 102 back to the gantry control board 24 that sync was successful.

Although the sync process 50 has been described as implemented in the master processor 31 and in the endpoint component processors 40, variants or portions of the sync process 50 may be implemented in other hardware, e.g., in the master switch 32 or specifically in the clock encoder 36.

Thus, aspects of the invention provide a method for synchronizing a plurality of components that are networked via a plurality of high speed switches. The method comprises frequency-locking to a master clock the component clocks of the plurality of components, and synchronizing to a master counter, driven by the master clock, a plurality of component counters driven by the plurality of component clocks, so that the frequency-locked component clocks drive the component counters in synchrony with the master counter. For example, frequency-locking may comprise encoding a sequence of master clock pulses from the master clock onto a clock stream transmitted among the plurality of components, and at each of the component clocks decoding a sequence of component clock pulses from the clock stream. Encoding a sequence of master clock pulses may comprise receiving an master stream at a clock encoder, receiving the sequence of master clock pulses at the clock encoder, and producing the clock stream from the clock encoder by modulating the master stream according to the sequence of master clock pulses. Decoding a sequence of component clock pulses may comprise at each component clock receiving the clock stream and demodulating the clock stream to produce the sequence of component clock pulses and to reproduce the master stream. Synchronizing may comprise encoding in the clock stream an instruction to set each component counter to match the master counter; encoding in the clock stream a plurality of instructions for each component to return a plurality of receipt times corresponding to the plurality of instructions; determining for each of the component counters a correction amount based on the plurality of receipt times returned by the corresponding component; and encoding in the clock stream an instruction to set each component counter to match the master counter adjusted by the correction amount corresponding to that component counter. In certain aspects, after synchronizing the component counters to the master counter, the frequency-locked component clocks maintain synchrony with zero overhead.

Other aspects of the invention provide a method for frequency-locking a component clock to a master clock. The method comprises defining a clock frequency and a master counter by periodically providing a master clock pulse from the master clock to a master processor. A clock encoder defines a clock stream by modulating the master clock pulse onto a master stream generated by the master processor at a bit transition rate greater than the clock frequency, and transmits the clock stream from the clock encoder to a clock decoder portion of the component clock, which recovers clock pulses from the clock stream. The method may further comprise maintaining at the master clock a master counter based on the master clock pulse; inserting in the master stream a first instruction to reset a component counter; and inserting in the master stream a second instruction to set the component counter to match the master counter. The method may further comprise inserting in the master stream a plurality of third instructions to obtain from the component clock a plurality of receipt times of those third instructions; and calculating, based on the plurality of receipt times of the plurality of third instructions, an average delay time from the master clock to the component clock. The method may further comprise inserting in the master stream a fourth instruction to set the component counter to match the master counter incremented by the average delay time from the master clock to the component clock. The master stream may, for example, encode CT scan data.

Embodiments of the invention provide a synchronous network time system, which comprises a master clock configured to generate a sequence of master clock pulses at a clock frequency; a master processor configured to receive the master clock pulses, maintain a master counter of the master clock pulses, and generate a master stream including instructions for initializing a component counter; a clock encoder configured to receive the master stream and the master clock pulses, and generate a clock stream by modulating the master clock pulses onto the master stream; a clock decoder configured to receive the clock stream, and extract from the clock stream the master stream and a sequence of component clock pulses; and a component clock configured to initialize and maintain a component counter based on the instructions from the master processor and the component clock pulses. The synchronous network time system may further comprise a first high speed data switch incorporating the clock encoder, and a second high speed data switch connected in communication with the clock decoder. The first high speed data switch may be configured to communicate the master stream to the second high speed data switch via the clock decoder, while the clock decoder is configured to provide the component clock pulses to the second high speed data switch, and the second high speed data switch is configured to reproduce the clock stream from the master stream and the component clock pulses. In certain embodiments, the master clock, the master processor, and the first high speed data switch are disposed on a gantry control board of a CT scanner, the master processor is configured to generate the master stream as a master stream also including a plurality of instructions for coordinating a plurality of gantry components of the CT scanner to perform at least one mode of CT scan, and the first high speed data switch is configured to transmit the clock stream to the plurality of gantry components; and the second high speed data switch is installed in communication between the clock decoder and a second clock decoder, which is installed as part of the component clock in communication with one of the plurality of gantry components. In certain embodiments, the clock decoder extracts the sequence of component clock pulses by demodulating the clock stream. In some embodiments, the master clock is configured to generate in the master stream a first instruction to reset the component counter and a second instruction to set the component counter to match the master counter. The master clock may also be configured to generate in the master stream a plurality of third instructions to obtain from the component clock a plurality of receipt times corresponding to the plurality of third instructions, and is further configured to calculate, based on the plurality of receipt times, an average delay time from the master clock to the component clock. Additionally, the master clock may be configured to generate in the master stream a fourth instruction to set the component counter to match the master counter incremented by the average delay time from the master clock to the component clock. The synchronous network time system may further comprise a phase-locked loop configured to remove jitter from the component clock pulses. In some embodiments, the component clock is configured to drive the component counter in synchrony with the master counter with zero overhead It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described embodiments, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:
1. A method for synchronizing a plurality of components that are networked via a plurality of high speed switches, said method comprising:
frequency-locking a plurality of component clocks of the plurality of components to a master clock;

synchronizing to a master counter, driven by the master clock, a plurality of component counters driven by the plurality of component clocks; and wherein the component clocks, when frequency-locked to the master clock, drive the component counters in synchrony with the master counter, and frequency-locking comprises encoding a sequence of master clock pulses from the master clock onto a clock stream transmitted among the plurality of components, and at each of the component clocks decoding a sequence of component clock pulses from the clock stream.

2. The method as claimed in claim 1, wherein encoding a sequence of master clock pulses comprises receiving a master stream at a clock encoder, receiving the sequence of master clock pulses at the clock encoder, and producing the clock stream from the clock encoder by modulating the master stream according to the sequence of master clock pulses.

3. The method as claimed in claim 2, wherein decoding a sequence of component clock pulses comprises at each component clock receiving the clock stream and demodulating the clock stream to produce the sequence of component clock pulses and to reproduce the master stream.

4. A method for synchronizing a plurality of components that are networked via a plurality of high speed switches, said method comprising:

frequency-locking a plurality of component clocks of the plurality of components to a master clock;

synchronizing to a master counter, driven by the master clock, a plurality of component counters driven by the plurality of component clocks; and wherein the component clocks, when frequency-locked to the master clock, drive the component counters in synchrony with the master counter, and synchronizing comprises:
  encoding in the clock stream an instruction to set each component counter to match the master counter;
  encoding in the clock stream a plurality of instructions for each component to return a plurality of receipt times corresponding to the plurality of instructions;
  determining for each of the component counters a correction amount based on the plurality of receipt times returned by the corresponding component; and
  encoding in the clock stream an instruction to set each component counter to match the master counter adjusted by the correction amount corresponding to that component counter.

* * * * *